United States Patent [19]

Hattori et al.

[11] Patent Number: 4,906,631

[45] Date of Patent: Mar. 6, 1990

[54] AMIDE DERIVATIVES AND ANTIALLERGIC AGENTS CONTAINING THE SAME

[75] Inventors: Shin Hattori, Yokohama; Makoto Takai, Hachioji; Kazuhiro Omori, Kawasaki; Shinji Ozawa, Tokyo; Toshio Wakabayashi, Tama, all of Japan

[73] Assignee: Terumo Kabushiki Kaisha, Tokyo, Japan

[21] Appl. No.: 238,604

[22] Filed: Aug. 31, 1988

Related U.S. Application Data

[62] Division of Ser. No. 939,135, Dec. 8, 1986, Pat. No. 4,795,752.

[30] Foreign Application Priority Data

Dec. 13, 1985 [JP] Japan .................. 60-280696

[51] Int. Cl.$^4$ .................. A61K 31/495; A61K 31/445; C07D 295/10; C07D 211/52
[52] U.S. Cl. .................. 514/255; 544/396; 514/327; 546/221
[58] Field of Search .................. 544/396; 514/255

[56] References Cited

U.S. PATENT DOCUMENTS

| | | | |
|---|---|---|---|
| 3,674,843 | 7/1972 | Shen et al. | 560/138 |
| 4,673,684 | 6/1987 | Wakabayashi et al. | 546/221 |
| 4,792,553 | 12/1988 | Hattori et al. | 544/396 |
| 4,795,752 | 1/1989 | Hattori et al. | 544/396 |

FOREIGN PATENT DOCUMENTS

| | | |
|---|---|---|
| 157420 | 10/1985 | European Pat. Off. . |
| 207901 | 1/1987 | European Pat. Off. ............ 544/396 |
| 214766 | 10/1985 | Japan . |

OTHER PUBLICATIONS

Greene, Protective Groups in Org. Synthesis, pp. 104–105 (1981).
Kametani et al., J. Het. Chem., vol. 12, No. 2 (1975), p. 259.
Hanselaer et al., Bull. Soc. Chim. Belg., vol. 92 (1983), p. 1029.
Ueda et al., Chem. Abst. 101-230573x (1984), "Benzhydrylpiperazine Derivatives, and Their Pharmaceutical Composition".
Arai et al., CA 103-16527h (1985) "Anti-Allergic Action of S-Lipoxygenase Inhibitors".
Uno et al., CA 105-226063w (1986), "Cinnamamide Derivatives and Salts".
Uno et al., CA 106-176422k (1987), "Preparation of Pyridylacrylamidoalkyl Piperazines . . . ".
Takai et al., CA 107-154084v (1987), "Preparation of Benzenealkaneamides and . . . ".
Ooe et al., CA 109-190042e (1988), "Preparation of 3.5-di-tert-butyl-4-hydroxycinnamamide . . . ".

Primary Examiner—Mukund J. Shah
Assistant Examiner—Cecilia Shen
Attorney, Agent, or Firm—Burns, Doane, Swecker & Mathis

[57] ABSTRACT

Novel amide derivatives are disclosed. As examples of said amide derivatives are mentioned 1-[2-[5-(3-methoxy-4-ethoxycarbonyloxyphenyl)-2,4-pentadienoyl]-aminoethyl]-4-benzhydroxypiperidine, 1-[2-[3-(3-methoxy-4-ethoxycarbonyloxyphenyl)-2-propenoyl]-4-benzhydroxypiperidine, 1-[3-[-(3-methoxy-4-ethoxycarbonyloxyphenyl)-2,4-pentadienoyl]aminopropyl]-4-benzhydrylpiperazine and the like. These amide derivatives are useful as antiallergic agents.

10 Claims, No Drawings

AMIDE DERIVATIVES AND ANTIALLERGIC AGENTS CONTAINING THE SAME

This application is a division of application Ser. No. 939,135, filed Dec. 9, 1986, now U.S. Pat. No. 4,795,752.

BACKGROUND OF THE INVENTION (1) Field of the Invention

The present invention relates to novel amide derivatives and antiallergic agents containing the same. The amide derivatives provided by the invention inhibit the passive cutaneous anaphylaxis reaction (PCA reaction, Naohiko Watanabe, Akio Kobayashi; Int. Archs Allergy Appl. Immun. 72, pp 53–58, S. Karger AG, Basel, 1983) in rats which is associated with the onset of allergy. The amide derivatives of the invention, therefore, are useful as an antiallergic agent.

(2) Description of the Prior Arts

A variety of compounds are known as possessing antiallergic activities, but there are no surely effective therapeutic agents, and development of drugs with improved efficacy is desired.

SUMMARY OF THE INVENTION

As a result of extensive studies on the synthesis of a variety of amide derivatives and their PCA reaction-inhibitory activities in rats, we have found that the amide derivatives according to the present invention have potent inhibitory activities of the PCA reaction in rats. The invention has been completed on the basis of the above finding.

It is an object of the invention to provide novel amide derivatives and antiallergic agents containing the same.

According to the invention, there are provided amide derivatives represented by the general formula (I)

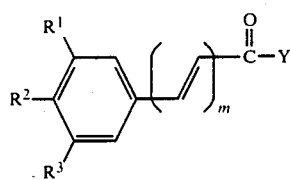

(I)

wherein $R^1$ and $R^2$ which may be the same or different respectively represent a lower alkoxyl group or a lower alkoxycarbonyl oxy group, $R^3$ represents a hydrogen atom or a lower alkoxyl group, m represents an integer of 1 or 2 and Y represents a group represented by the formula(II)

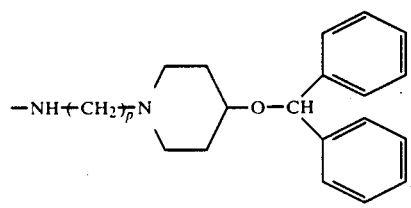

(II)

wherein p represents an integer of from 2 to 4 or a group represented by the formula (III)

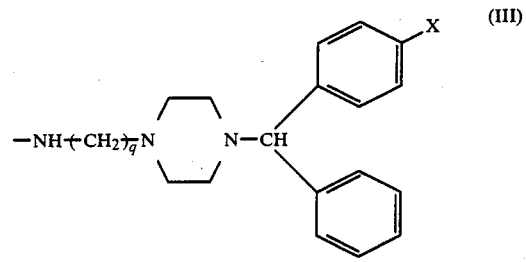

(III)

wherein X represents a hydrogen atom, a halogen atom or a methoxy group and q represents an integer of from 2 to 4.

Further, according to the invention there are provided antiallergic agents containing an amide derivative represented by the above-mentioned formula (I).

Further, according to the invention there is provided a therapeutic method of allergic conditions which comprises administering animals with an effective dose of an amide derivative represented by the above-mentioned formula (I).

DETAILED DESCRIPTION OF THE INVENTION

The lower alkoxyl group as defined herein for the substituent in the above-mentioned formula (I) means a straight or branched chain alkoxyl group having from 1 to 4 carbon atoms, which is preferably methoxy, ethoxy, n-propoxy or isopropoxy. As the halogen atom is preferred fluorine, chlorine or bromine.

The amide derivatives represented by the above mentioned formula (I) are produced by reacting a reactive derivative of a carboxylic acid represented by the formula (IV)

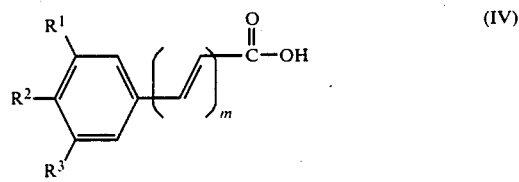

(IV)

wherein $R^1$, $R^2$, $R^3$ and m have the same meanings as defined above with an amine derivative represented by the formula (V)

H—Y  (V)

wherein Y has the same meaning as defined above.

As the reactive derivative of the above-mentioned carboxylic acids (IV) is preferably employed an acid halide, for example, the chloride or bromide, an anhydride or a mixed acid anhydride, for example, the mixed acid anhydride with ethylcarbonic acid.

The above-described reaction is carried out by a method known per se. For example, to a solution of a reactive derivative of the carboxylic acid (IV) dissolved in an appropriate organic solvent such as, for example, dichloromethane or chloroform is added the amine derivative (V), and the mixture is reacted at room temperature for several hours. The desired product (I) is isolated from the reaction mixture by conventional procedures and purified by such means as recrystallization or column chromatography.

The amide derivatives of the invention are used as an antiallergic agent. The dosage, which may be variable depending upon conditions of the disease, is generally 1–1000 mg and preferably 10–500 mg per day in adults, divided into one to three doses as required for the conditions. The administration may be in any suitable form, oral administration being particularly preferred but intravenous administration also being acceptable.

The compound of the invention may be administered as the active component or one of the active components either alone or in admixture with pharmaceutical carriers or excipients formulated by a conventional process into tablets, sugar-coated tablets, powders, capsules, granules, suspension, emulsion, injectable solution or the like. As examples of the carrier or excipient are mentioned calcium carbonate, calcium phosphate, starch, glucose, lactose, dextrin, alginic acid, mannitol, talc, and magnesium stearate.

Examples and a test example will be given below to describe in more details, but they are not intended to limit the invention in any way.

EXAMPLE 1

To a solution of 15 g (68.1 mmol) of 5-(3-methoxy-4-hydroxyphenyl)-2,4-pentadienoic acid in 400 ml of dichloromethane cooled to 0° C. was added 21 ml (150 mmol) of triethylamine followed by addition of 14.3 ml (150 mmol) of ethylcarbonyl chloride. The mixture was stirred at 0° C. for one hour.

Separately, to an ethanol solution (400 ml) of 30 g (68.1 mmol) of 1-(2-phthaloylaminoethyl)-4-benzhydroxypiperidine was added 4.26 g (68.1 mmol) of 80% hydrazine hydrate, and the mixture was heated under reflux for 2 hours. The reaction mixture was concentrated under reduced pressure, and to the residue thus produced was added 400 ml of dichloromethane. The mixture was added to the reaction mixture prepared above. The resulting mixture was stirred at room temperature for 14 hours.

The reaction mixture was filtered, and the filtrate was washed successively with 1N-hydrochloric acid, water and saturated aqueous sodium hydrogen carbonate. The organic layer was dried over sodium sulfate and concentrated under reduced pressure. The residue thus obtained was recrystallized from ethanol. There was afforded 27.8 (47.7 mmol) of 1-[2-[5-(3-methoxy-4-ethoxycarbonyloxyphenyl)-2,4-pentadienoyl]aminoethyl]-4-benzhydroxypiperidine. Spectrophotometric data of the product support the structure (VI) shown below.

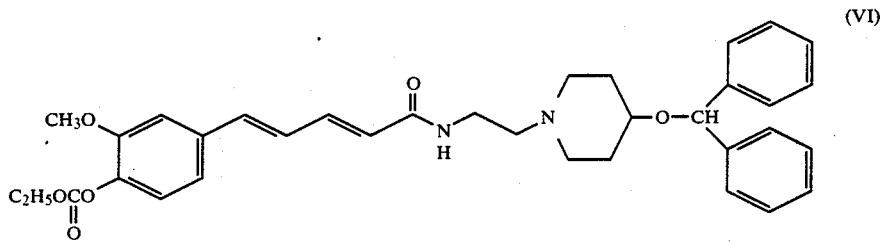

(VI)

PMR (CDCl$_3$)δ: 1.33(3H, t, J=8Hz), 1.52–3.0
(10H, m), 3.16–3.78(3H, m), 3.78(3H, s),
4.22(2H, q, J=8Hz), 5.42(1H, s), 5.88(1H,
d, J=15Hz), 6.55–7.67(16H, m)
IR:ν$_{max}^{CHCl_3}$ (cm$^{-1}$): 3400, 1762, 1660, 1615,
1510, 1255.

EXAMPLE 2

To a solution of 2.27 g (11.7 mmol) of ferulic acid in 100 ml cf dichloromethane cooled to 0° C. was added 3.5 ml of triethylamine followed by addition of 2.4 ml (25 mmol) of ethyl chlorocarbonate. The mixture was stirred at 0° C. for one hour. Separately, to an ethanol solution (100 ml) of 5 g (11.3 mmol) of 1-(2-phthaloylaminoethyl)-4-benzhydroxypiperidine was added 1.07 g (17 mmol) of 80% hydrazine hydrate. The mixture was heated under reflux for 2 hours. The reaction mixture was concentrated under reduced pressure, and to the residue was added 100 ml of dichloromethane followed by addition of th reaction mixture prepared above. The resulting mixture was stirred at room temperature for 14 hours. The reaction solution was filtered, and the filtrate was washed successively with 1N-hydrochloric acid, water and saturated aqueous sodium hydrogen carbonate. The organic layer was dried over sodium sulfate and concentrated under reduced pressure. The residue thus obtained was recrystallized from ethanol. There was obtained 4.24 g (7.6 mmol) of 1-[2-[3-(3-methoxy-4-ethoxycarbonyloxyphenyl)-2-propenyoyl]-aminoethyl]-4-benzhydroxypiperidine. Spectrophotometric data of the product support the structural formula (VII) shown below.

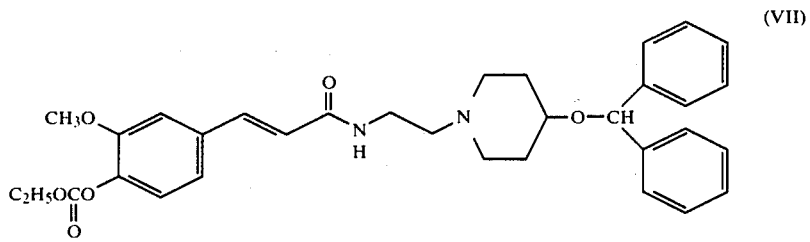

(VII)

PMR (CDCl₃)δ: 1.35(3H, t, J=8Hz), 1.50-3.0
(10H, m), 3.20-3.70(3H, m), 3.78(3H, s),
5.45(1H, s), 6.23(1H, d, J=16Hz), 6.70-
7.60(14H, m).
IR:$\nu_{max}^{CHCl_3}$ (cm⁻¹): 3400, 1765, 1660, 1610, 1260.

EXAMPLE 3

To a solution of 5 g (22.7 mmol) of 5-(3-methoxy-4-hydroxyphenyl)-2,4-pentadienoic acid in 500 ml of dichloromethane cooled to 0° C. was added 6.7 ml (47.8 mmol) of triethylamine followed by addition of 4.6 ml (47.8 mmol) of ethylchlorocarbonate. The mixture was stirred at 0° C. for one hour.

Separately, to an ethanol solution (400 ml) of 10 g (22.7 mmol) of 1-(3-phthaloylaminopropyl)-4-benzhydrylpiperazine was added 2.28 g (36.4 mmol) of 80% hydrazine hydrate. The mixture was heated under reflux for 2 hours. To the residue obtained by concentration of the reaction solution under reduced pressure was added 400 ml of dichloromethane followed by addition of the reaction mixture prepared above. The mixture was stirred at room temperature for 14 hours. The reaction mixture was filtered, and the filtrate was washed successively with 1N-hydrochloric acid, water and saturated aqueous sodium hydrogen carbonate. The organic layer was dried over sodium sulfate and concentrated under reduced pressure. The residue thus obtained was recrystallized to afford 9.5 g (16.3 mmol) of 1-[3-[5-(3-methoxy-4-ethoxycarbonyloxyphenyl)-2,4-pentadienoyl]aminopropyl]-4-benzhydrylpiperazine.
Spectrophotometric data of the product support the structural formula (VIII) shown below.

EXAMPLE 4

To a solution of 180 mg (1 mmol) of caffeic acid (3,4-dihydroxysuccinic acid) in 10 ml of dichloromethane cooled to 0° C, was added 303 mg (3 mmol) of triethylamine followed by addition of 326 mg (3 mmol) of ethylcarbonyl chloride. The mixture was stirred at 0° C. for 3 hours.

Separately, to a 10 ml-ethanol solution of 440 mg (1 mmol) of 1-(2-phthaloylaminoethyl)-4-benzhydroxypiperidine was added 63 mg (1 mmol) of 80% hydrazine hydrate, and the mixture was heated under reflux for 2 hours. The reaction solution was concentrated under reduced pressure, and to the residue thus obtained was added 10 ml of dichloromethane followed by addition of the reaction solution prepared above. The mixture was stirred at room temperature for 2 hours.

The reaction solution was filtered, and the filtrate was washed successively with 1N-hydrochloric acid, water and saturated aqueous sodium hydrogen carbonate. The organic layer was dried over sodium sulfate and concentrated under reduced pressure. The residue thus obtained was subjected to silica gel column chromatography. There was afforded from a fraction eluted with chloroform-methanol (50:1) 311 mg (0.5 mmol) of 1-[2-[3-(3,4-diethoxycarbonyl-oxyphenyl)-propenyl-]aminoethyl]-4-benzhydroxypiperidine. Spectropho-

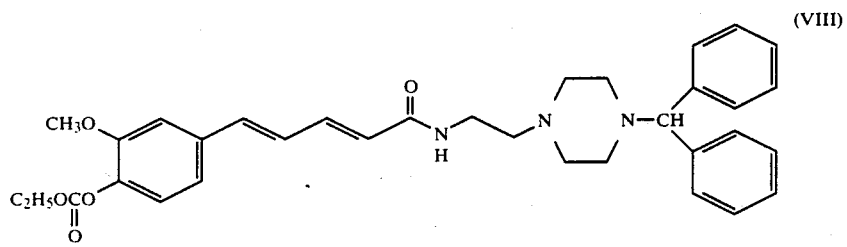
(VIII)

PMR (d₆-acetone)δ: 1.35(3H, t, J=8Hz), 3.75
(2H, q, J=6Hz), 2.41(10H, b,s), 3.33(2H,
t, J=6Hz), 3.85(3H, s), 4.22(1H, s), 4.25
(2H, q, J=8Hz), 6.18(1H, d, J=15Hz),
6.60-7.70(16H, m).
IR:$\nu_{max}^{CHCl_3}$ (cm⁻¹): 3400, 1760, 1660, 1610.

metric data of the product support the structural formula (IX) shown below.

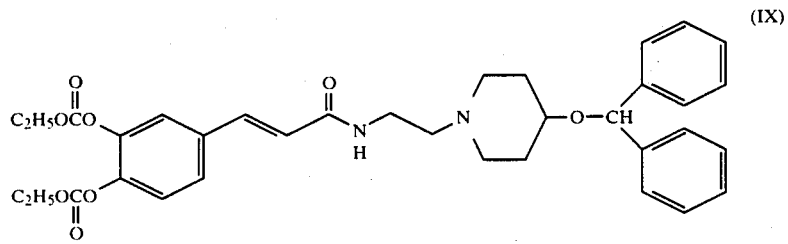
(IX)

PMR (CDCl₃)δ: 1.33(6H, t, J=8Hz), 1.60–4.0
(13H, m), 4.25(4H, q, J=8Hz), 5.37(1H,
s), 6.52(1H, d, J=15Hz), 7.0–7.8(14H, m).
IR:ν$_{max}^{CHCl_3}$ (cm⁻¹): 3400, 1765, 1670, 1630, 1260.

EXAMPLE 5

To a solution of 206 mg (1 mmol) of 5-(3,4-dihydroxyphenyl)-2,4-pentadienoic acid in 10 ml of dichloromethane cooled to 0° C. was added 303 mg (3 mmol) of triethylamine followed by addition of 326 mg (3 mmol) of ethyl chlorocarbonate. The mixture was stirred at 0° C. for 3 hours.

Separately, to a 10 ml of an ethanol solution of 440 mg (1 mmol) of 1-(2-phthaloylaminoethyl)-4-benzhydroxypiperidine was added 63 mg (1 mmol) of 80% hydrazine hydrate. The mixture was heated under reflux for 2 hours. To the residue obtained by concentration of the reaction solution under reduced pressure was added 10 ml of dichloromethane followed by addition of the reaction solution prepared above. The mixture was stirred at room temperature for 2 hours.

The reaction solution was filtered, and the filtrate was washed successively with 1N-hydrochloric acid, water and saturated aqueous sodium hydrogen carbonate. The organic layer was dried over sodium sulfate and concentrated under reduced pressure. The residue thus obtained was subjected to silica gel column chromatography. There was afforded from a fraction eluted with chloroform-methanol (50:1) 350 mg (0.54 mmol) of 1-[2-[5-(3,4-diethoxycarbonyloxyphenyl)-2,4-pentadienoyl]aminoethyl]-4-benzhydroxypiperidine. Spectrophotometric data of the product support the structural formula (X) shown below.

Blue containing 1 mg of the DNP-ascaris from the tail. After 30 minutes, the animal was sacrificed by bleeding and the portion of the skin with the dye exuded was cut off. The cut skin was treated with 1N-KOH solution, and the dye was extracted by adding 9 ml of 0.6N-phosphoric acid-acetone (5:13) mixture. The supernatant from centrifugal separation was measured for absorbency at 620 nm to determine amount of the dye. Percent inhibition at each of the concentrations of the amide derivatives was calculated in comparison with amount of the dye for control group. 50% Inhibitory concentration (ID₅₀) of the amide derivatives against exudation of the dye was determined from the percent inhibition-concentration graph. Results are shown in Table-I. Percent inhibition of tranilast, an antiallergic agent commercially available from Kissei Pharmaceutical Co., Ltd. under the trade name of Rizaben against PCA reaction was also shown in Table-I. As shown in Table-I, the amide derivatives of the invention produced high PCA reaction-inhibitory effects.

TABLE I

| | PCA reaction-inhibitory effects in rats | | |
|---|---|---|---|
| Test compound Example No. | Concentration (mg/kg) | Inhibition (%) mean ± SE | ID₅₀ (mg/kg) |
| 1 | 3 | 26 ± 15 | 10 |
| | 10 | 51 ± 18 | |
| | 30 | 71 ± 6 | |
| 2 | 3 | 20 ± 15 | 15 |
| | 10 | 41 ± 16 | |
| | 30 | 64 ± 5 | |
| 3 | 10 | 19 ± 14 | 55 |
| | 30 | 38 ± 15 | |
| | 100 | 63 ± 5 | |
| 4 | 3 | 22 ± 14 | 12 |
| | 10 | 46 ± 10 | |
| | 30 | 68 ± 7 | |
| 5 | 3 | 30 ± 16 | |
| | 10 | 55 ± 10 | |
| | 30 | 75 ± 4 | |
| Control | 100 | 37 ± 8 | >300 |
| | 200 | 40 ± 10 | |
| | 300 | 42 ± 5 | |

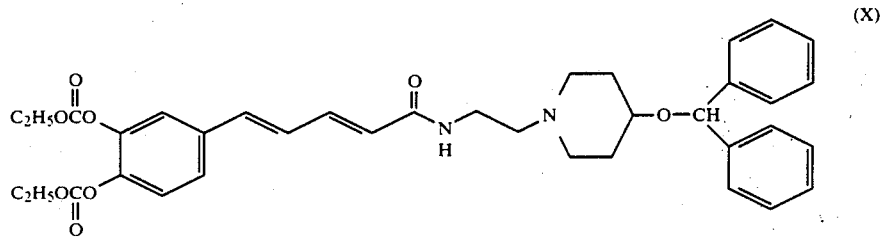

(X)

PMR (CDCl₃)δ: 1.34(6H, t, J=8Hz), 1.60–4.0
(13H, m), 4.28(4H, q, J=8Hz), 5.40(1H, s),
6.5–7.8(17H, m).
IR:ν$_{max}^{CHCl_3}$ (cm⁻¹): 3400, 1765, 1660, 1610, 1260.

TEST EXAMPLE

DNP-ascaris (1 mg) prepared by combining a swine ascaris extract with 2,4-dinitrophenyl sulfate was mixed with 20 mg of aluminum hydroxide gel. The mixture was administered to rats subcutaneously on the back, and at the same time the animals were intraperitoneally given 2×10¹⁰ dead Bordetella pertussis respectively. The same procedures were repeated after 14 days, and blood sample was obtained after 21 days to produce antisera.

Female Sprague-Dawley strain rats (8 weeks old were sensitized by subcutaneously administering 0.1 ml of 1:256 diluted antisera (titer=1024) respectively on the grained back. After 48 hours, groups of four rats were orally given the amide derivatives produced in the examples above at various concentrations. After one hour, the rats were challenged by intravenously administering a 0.5% physiological saline solution of Evans It has been confirmed that amide derivatives of the invention not shown in Table-I also possess PCA reaction-inhibitory effects in rats.

Acute Toxicity

An acute toxicity test was conducted using male ICR mice (5 weeks old) by oral administration. $LD_{50}$ was 1000 mg/kg or higher with every compound of the invention to demonstrate high safety margin as compared with the effective dose.

What is claimed is:

1. An amide derivative represented by the formula (I)

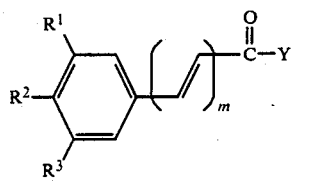
(I)

wherein $R^1$ represents a lower alkoxy group or a lower alkoxycarbonyloxy group, $R^2$ represents a lower alkoxycarbonyloxy group, $R^3$ represents a hydrogen atom, m represents an integer of 1 or 2 and Y represents a group represented by the formula (III)

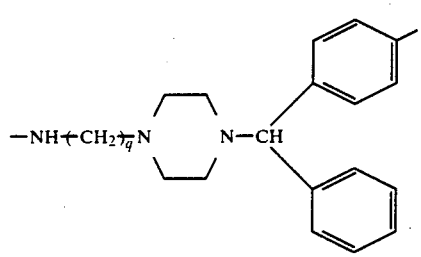
(III)

wherein X represents a hydrogen atom, a halogen atom or a methyoxy group and q represents an integer of from 2 to 4.

2. An amide derivative according to claim 1 wherein $R^1$ and $R^2$ respectively represent an ethoxycarbonyloxy group and $R^3$ represents a hydrogen atom.

3. An amide derivative according to claim 1 wherein $R^1$ represents a lower alkoxyl group, $R^2$ represents a lower alkoxycarbonyloxy group and $R^3$ represents a hydrogen atom.

4. An amide derivative according to claim 1 wherein $R^1$ and $R^3$ respectively represent a lower alkoxyl group and $R^2$ represents a lower alkoxycarbonyloxy group.

5. A method for the therapy of allergic conditions which comprises administering to animals an effective dose of an amide derivative of claim 1 to treat allergic conditions.

6. The method according to claim 6 wherein $R^1$ and $R^2$ respectively represent an ethoxycarbonyloxy group and $R^3$ represents a hydrogen atom.

7. The method according to claim 6 wherein $R^1$ represents a lower alkoxyl group, $R^2$ represents a lower alkoxycarbonyloxy group and $R^3$ represents a hydrogen atom.

8. A pharmaceutical composition of matter for treatment of allergic conditions, said method comprising administering to animals in need of such treatment an effective amount to treat allergic conditions of an amide derivative represented by the formula (I)

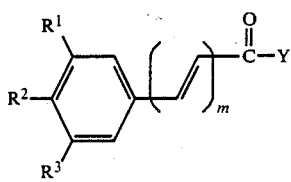
(I)

wherein $R^1$ represents a lower alkoxy group or a lower alkoxycarbonyloxy group, $R^2$ represents a lower alkoxycarbonyloxy group, $R^3$ represents a hydrogen atom, m represents an integer of 1 or 2 and Y represents a group represented by the formula (III)

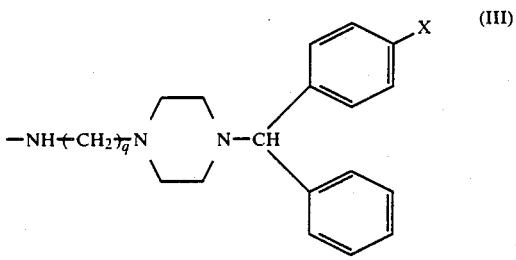
(III)

wherein X represents a hydrogen atom, a halogen atom or a methoxy group and q represents an integer of from 2 to 4 and a pharmaceutically acceptable carrier therefor.

9. The composition according to claim 8 wherein $R^1$ and $R^2$ respectively represent an ethoxycarbonyloxy group and $R^3$ represents a hydrogen atom.

10. The composition according to claim 8 wherein $R^1$ represents a lower alkoxy group, $R^2$ represents a lower alkoxycarbonyloxy group and $R^3$ represents a hydrogen atom.

* * * * *